United States Patent

Demarais et al.

[11] Patent Number: 6,097,978
[45] Date of Patent: Aug. 1, 2000

[54] MEASUREMENT CONFIRMATION DEVICES AND METHODS FOR FLUOROSCOPICALLY DIRECTED SURGERY

[75] Inventors: Denise M. Demarais, Sunnyvale; Michael A. Evans, Palo Alto; Glen R. Davis, Sunnyvale; Sascha K. Zarins, Stanford; Allan R. Will, Atherton, all of Calif.

[73] Assignee: Medtronic Inc., Minneapolis, Minn.

[21] Appl. No.: 08/887,550

[22] Filed: Jul. 3, 1997

Related U.S. Application Data

[60] Provisional application No. 60/025,231, Jul. 12, 1996.

[51] Int. Cl.$^7$ .................................................. A61B 5/05
[52] U.S. Cl. ........................ 600/429; 378/163; 378/205
[58] Field of Search .................................. 600/407, 429, 600/414, 417, 426; 378/204, 205, 163

[56] References Cited

U.S. PATENT DOCUMENTS

| | | | |
|---|---|---|---|
| 1,904,234 | 4/1933 | Hoskin et al. | 378/163 |
| 3,812,842 | 5/1974 | Rodriguez . | |
| 4,583,538 | 4/1986 | Onik et al. | 128/303 |
| 4,930,525 | 6/1990 | Palestrant | 128/898 |
| 5,047,050 | 9/1991 | Arpesani | 623/1 |
| 5,189,690 | 2/1993 | Samuel . | |
| 5,239,982 | 8/1993 | Trauthen | 128/4 |
| 5,419,324 | 5/1995 | Dillow | 128/653 |
| 5,489,295 | 2/1996 | Piplani et al. | 623/1 |
| 5,752,522 | 5/1998 | Murphy | 600/587 |

FOREIGN PATENT DOCUMENTS

| | | | |
|---|---|---|---|
| 0684022 | 4/1995 | European Pat. Off. | A61F 2/06 |
| 0714636 | 9/1995 | European Pat. Off. | A61B 19/00 |
| 0723786 | 1/1996 | European Pat. Off. | A61M 25/00 |
| WO 96/37616 | 10/1997 | WIPO | A61F 2/06 |

*Primary Examiner*—Brian L. Casler

[57] ABSTRACT

The present invention provides methods and apparatus for measuring and/or marking the internal features of a patient body when those features are viewed under fluoroscopy or another medical imaging modality. Although suitable for the physiological measurement of many body lumens, including the intestines, the urethra, and the like, the present invention will find its most immediate use in the measurement of vascular lesions, particularly vascular aneurysms adjacent the aortoiliac junction and other bifurcations. The positions and bend angles of such branching body lumens can be accurately mapped on a panel which remains outside the patient body. By imaging the patient through the panel, and by providing markings on the panel which give a bright contrast when imaged, the panel provides a guide that highlights the length, position, and geometry of the luminal lesion. The guide may be tailored for the specific bifurcated prosthesis to be deployed, and can also graphically illustrate the safe and effective range of target positions in which to deploy the prosthesis.

13 Claims, 6 Drawing Sheets

MEASUREMENT CONFIRMATION DEVICES AND METHODS FOR FLUOROSCOPICALLY DIRECTED SURGERY

CROSS REFERENCE TO RELATED APPLICATIONS

This application is a continuation-in-part of, and claims priority from, U.S. Provisional Patent Application Ser. No. 60/025,231, filed Jul. 12, 1996, the full disclosure of which is herein incorporated by reference in its entirety.

BACKGROUND OF THE INVENTION

1. Field of the Invention

The present invention relates generally to the field of medical imaging, and particularly to measuring and marking of the dimensions of internal physiological characteristics. In one particular aspect, the invention provides fluoroscopic guides and methods for modeling the geometry of endoluminal prostheses within curving and/or branching body lumens such as blood vessels.

To properly treat many bodily diseases or abnormalities, certain physiologic characteristics, such as the size of a particular body member, often need to be determined. Examples of therapies which depend on accurate measurements include the treatment of vascular lesions, stenosed regions, and particularly vascular aneurysms, which often require the endoluminal placement of tubular prostheses, such as grafts, stents, stent-grafts, and other structures. Before the prothesis is placed in the vascular anatomy, the size of the lesion is measured so that a properly sized prosthesis can be selected.

Vascular aneurysms are the result of abnormal dilation of a blood vessel, usually resulting from disease and/or genetic predisposition, which can weaken the arterial wall and allow it to expand. While aneurysms can occur in any blood vessel, most occur in the aorta and peripheral arteries, with the majority of aortic aneurysms occurring in the abdominal aorta, usually beginning below the renal arteries and often extending into one or both of the iliac arteries.

Aortic aneurysms are most commonly treated in open surgical procedures where the diseased vessel segment is bypassed and repaired with an artificial vascular graft. While considered to be an effective surgical technique, particularly considering the alternative of a usually fatal ruptured abdominal aortic aneurysm, conventional vascular graft surgery suffers from a number of disadvantages. The surgical procedure is complex and requires experienced surgeons and well equipped surgical facilities. Even with the best surgeons and equipment, however, patients being treated frequently are elderly and weakened from cardiovascular and other diseases, reducing the number of eligible patients. Even for eligible patients prior to rupture, conventional aneurysm repair has a relatively high mortality rate, usually from 2% to 10%. Morbidity related to the conventional surgery includes myocardial infarction, renal failure, impotence, paralysis, and other conditions. Additionally, even with successful surgery, recovery takes several weeks, and often requires a lengthy hospital stay.

In order to overcome some or all of these drawbacks, endovascular prosthesis placement for the treatment of aneurysms has been proposed. Although very promising, many of the proposed methods and apparatus suffer from undesirable limitations. In particular, proper sizing and positioning of endovascular prostheses can be problematic.

Before endoluminal prosthetic deployment, it is necessary to first determine the appropriate size for the prosthesis so that the prosthesis will properly fit within the body lumen. For instance, in the case of vascular aneurysms, it is desirable to determine the length of the aneurysm so that the prosthesis will be long enough to extend through the diseased area of the vessel. In this way, both ends of the prosthesis can be anchored to a healthy vessel wall.

Current methods for determining the length of an effected body lumen employ fluoroscopy. To determine the length of a vessel using fluoroscopy, a catheter is inserted into the vessel and a contrast agent is injected into the vessel through the catheter. The blood flow carries the contrast agent along the vessel so that the vessel can be radiographically imaged with a fluoroscope. The fluoroscope produces a planar (or two dimensional) image of the vessel which can be evaluated to determine the existence of a diseased or abnormal area within the vessel. The length of the diseased or abnormal area is then estimated by measuring the length of the diseased area on the radiographic image. Unfortunately, accurate linear measurement of these complex three dimensional bodies is difficult to provide when using this known technique.

U.S. patent application Ser. No. 08/380,735, filed Jan. 30, 1995, now abandoned (Attorney Docket No. 016380-001600), and Ser. No. 08/435,288, filed May 4, 1995 now U.S. Pat. No. 5,752,522 (Attorney Docket No. 016380-002900), the full disclosures of which are herein incorporated by reference, describe endoluminal methods for directly measuring lumenal lengths and cross-sections which help to avoid the inaccuracy of measuring curving, three dimensional blood vessels with the known two dimensional fluoroscopic process. By introducing direct measurement devices into the curving blood vessels, and by placing radiopaque markers at either end of a vascular region to measure length, or radially expanding a balloon or other occlusion device until flow is substantially blocked to measure cross-section, these direct measurement devices significantly enhance the accuracy of endoluminal measurements.

Although the direct luminal measurement devices and methods described above represent significant advancements in accurate luminal measurements for placement of endoluminal prostheses and other devices, known methods for subsequently positioning those devices based on these measurements still suffer from certain drawbacks. In particular, once measurements have been made and luminal prosthetic deployment is under way, work in connection with the present invention has shown that accurate positioning of even a correctly sized prosthesis can prove difficult. This is particularly true when positioning bifurcated prostheses extending from the abdominal aorta into the two iliac arteries for treatment of an aortoiliac aneurysm. The bifurcated prosthesis will preferably seal off the aneurysm, but will not obstruct flow to the renal or hypogastric arteries. Unfortunately, the geometry of the aortoiliac junction varies widely between patients, and the position of the prosthesis may shift during deployment. The interaction between the flexible or semi-flexible prosthesis and the complex lumenal geometry can be difficult to visualize, making the deployed prosthetic geometry somewhat unpredictable. Further complicating the situation, direct measurement devices are often removed to avoid interfering with prosthetic deployment, leaving the physician with little guidance as deployment progresses. Finally, where planar measurements are made, the scope often distorts the imaged body structures so that even relative measurements taken from different portions of the image, or along different measurement axis, are highly inaccurate.

In light of the above limitations and disadvantages, it is desirable to provide improved methods and devices to guide endoluminal positioning and placement of tubular prostheses. It would be particularly desirable to provide a simple, reliable reference and measurement device for use during fluoroscopically directed, minimally invasive procedures. It would further be desirable if such improved devices and methods were adaptable to the wide variety of vascular geometries exhibited by patients in need of bifurcated or straight endoluminal prostheses.

2. Description of the Background Art

As previously described, methods and apparatus for direct measurement of the length and cross-section of endoluminal lesions are described in co-pending U.S. patent application Ser. No. 08/380,735, and U.S. Pat. No. 5,752,522 (Attorney Docket Nos. 016380-001600 and 016380-002900). A catheter depth gauge and method of use are described in U.S. Pat. No. 5,239,982. A reference scale in the form of adhesive tape having radiopaque measurement markers is commercially available under the tradename LeMaitre Glow 'N Tell Tape from Vascutech, Inc.

SUMMARY OF THE INVENTION

The present invention provides methods and apparatus for measuring and/or marking the internal features of a patient's body when those features are viewed under fluoroscopy or another medical imaging modality. Although suitable for the physiological measurement of many internal structures, particularly body lumens such as the intestines, the urethra, and the like, the present invention will find its most immediate use in the measurement of vascular lesions, including vascular aneurysms adjacent the aortoiliac junction and other bifurcations. Advantageously, the positions and bend angles of such branching body lumens can be accurately mapped on a panel which remains outside the patient body. By imaging the patient through the panel, and by providing markings on the panel which have a sharp contrast when imaged, the panel provides a guide that highlights the length, position, and geometry of the luminal lesion. Advantageously, this guide may be tailored for a specific bifurcated prosthesis to be deployed, and can be used to model the prosthesis and visually predict its deployed shape. The guide may also graphically illustrate the safe and effective range of target positions for the specific patient in which the prosthesis will be deployed.

In a first aspect, the present invention provides a position guide for internal anatomical features of a patient body, the guide comprising a panel which defines a reference plane. The panel includes a radiotranslucent material through which the patient body may be imaged. A first gauge portion is supported by the panel and includes radiopaque markings. A second gauge portion extends from the first gauge portion and also has radiopaque markings. The second gauge portion is movable relative to the first gauge portion along the reference plane. Advantageously, these first and second gauge portions may be aligned along the image of a curving or complex internal anatomical feature, such as a branching body lumen.

Generally, the first gauge portion will define an axis from which the second gauge portion is laterally deflectable, so that the markings of the first and second gauge portions can be aligned along axially curving vessels. A guide having a third gauge portion which extends from the first portion is particularly useful for marking the paths of branching arteries during deployment of bifurcated endoluminal prostheses. The markings on the gauge portions will often comprise measurement scales and/or target position ranges. Such a guide not only provides measurements of anatomical features and locations, but can also model the deployed geometry which the flexible or semi-flexible bifurcated prosthesis will assume once it is implanted.

In another aspect, the present invention provides a curving body lumen guide comprising a panel having a major surface defining a reference plane and an edge adjacent the major surface. The panel comprises a radiotranslucent material. A first gauge portion is supported by the panel, the first gauge portion having radiopaque markings which define a measurement axis. The second gauge portion extends from the first gauge portion, and also has radiopaque markings. This second gauge portion is laterally deflectable along the reference plane relative to the measurement axis of the first gauge portion. A deflecting mechanism extends from the second gauge portion to the end of the panel, allowing the markings of the first and second gauge portions to be aligned along the curving body lumen while the body lumen is imaged through the panel. Often times, the first gauge portion will also be movable relative to the panel, typically being axially slidable.

In another aspect, the present invention provides a measurement verification catheter for use with a bifurcated endoluminal prosthesis delivery system. The delivery system includes a prosthesis and a delivery sheath. The prosthesis has a first end, a second end, and a branch therebetween, and is disposable within the delivery sheath for introduction and positioning of the prosthesis within the vascular system. The catheter comprises an elongate body having a proximal end and a distal end. A distal position marker is near the distal end of the elongate body, the distal marker being visible under imaging. A proximal marker is disposed proximally of the distal marker by a distance corresponding to a length between the first and second ends of the prosthesis. A branch marker is disposed between the distal and proximal markers, the branch marker being proximal of the distal marker by a distance corresponding to a length between the branch of the prosthesis and one of the first and second ends of the prosthesis. In use, such a measurement verification catheter may be easily introduced and positioned across the luminal lesion after selection of an appropriately sized prosthesis, and prior to actual deployment of the prosthesis. As the catheter can be made quite small and flexible, it will be possible to follow a pre-positioned guidewire with very little difficulty. Hence, the present catheter provides simple and effective prosthesis size verification, and may therefore be included in a prosthetic delivery system and/or kit.

In another aspect, the present invention provides a method comprising imaging a vascular system of a patient body through a panel disposed adjacent the patient body. Markings of a first gauge portion on the panel are aligned with a first target site of the vascular system. Markings of a second gauge portion on the panel are aligned with a second target site of the vascular system. Although a vascular axis at the first target site is disposed at an angle relative to a vascular axis at the second target site, the markings of the first and second gauge portions will substantially indicate an axial length along the vascular system between the first and second target sites. Often times, markings of a third gauge portion on the panel are aligned with a third target site of the vascular system which is also disposed at an angle relative to the first site. Hence, the markings of the gauge portions can indicate axial lengths along separate branches of the vascular system. Ideally, these first, second, and third gauge portions are then used as a lumenal map for the deployment of a bifurcated endoluminal prosthesis between the first, second, and third sites.

DETAILED DESCRIPTION OF THE SPECIFIC EMBODIMENT

Figure 1:
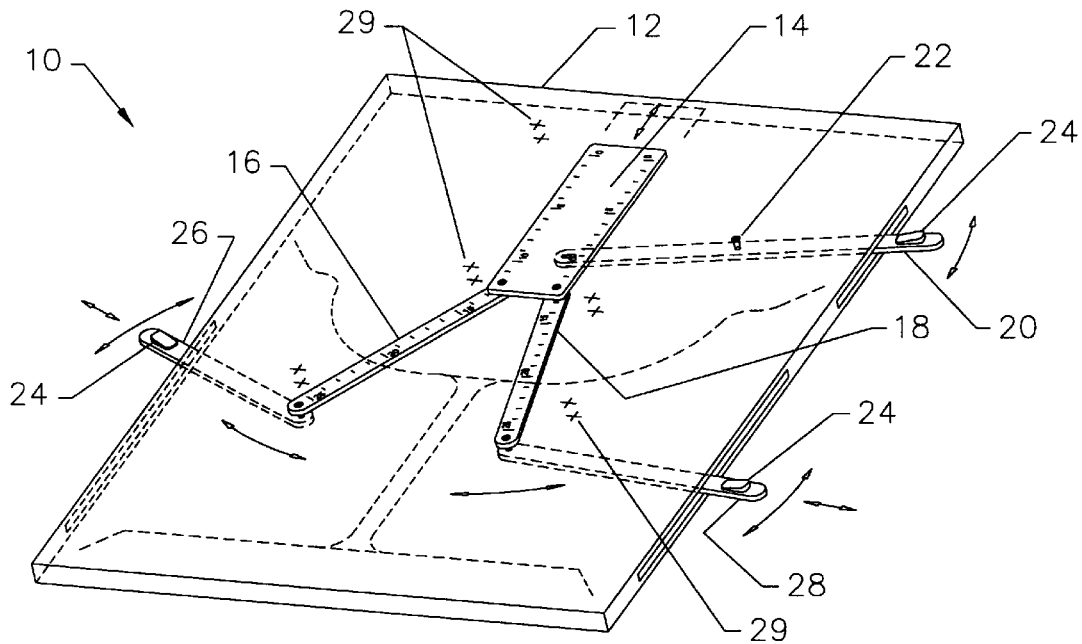
FIG. 1 is a perspective view of a guide for deployment of a bifurcated endoluminal prosthesis, the guide having three articulated gauge portions which may be manipulated within a radiotranslucent panel to fluoroscopically align the gauge portions along a bifurcated body lumen, according to the principles of the present invention.

Referring now to FIG. 1, a bifurcated luminal guide 10 includes a panel 12 and first, second, and third gauge portions 14, 16, and 18. In the exemplary embodiment, these gauge portions are movably disposed within the panel 12. To allow movement of the gauge portions, the panel will be formed as a multi-level laminated structure having gaps between the upper and the lower surfaces.

First gauge portion 14 slides axially along its length when manipulated by a first lever 20. Specifically, first lever 20 pivots about a pivot point 22, while first gauge portion 14 slides axially relative to the surrounding panel structure. A simple tapered wedge 24 is slidable along the lever 20. By sliding wedge 24 against the adjacent panel structure, the axial position of the first guide portion can be locked in place.

A second lever 26 laterally deflects the second gauge portion 16 to the desired position, and also includes a locking wedge 24 to prevent the gauge from moving inadvertently. Similarly, a third lever 28 allows independent manipulation of third gauge portion 18. Conveniently, the first, second, and third levers allow the gauge portions to be manipulated from the edge of panel 12, which greatly facilitates aligning the gauge with the fluoroscopic image of an abdominal aortic aneurysm or other target body structure.

Also illustrated in FIG. 1 are several parallax indicators 29. Each parallax indicator includes a first radiopaque marker (here shown as a crosshair) near the upper cover of the panel, and a second radiopaque marker at a distance from the plane of the cover, preferably being near the bottom of the panel structure. Typically, these markers will be aligned when the panel is imaged normally to the plane of the panel cover. As the markers are at different depths, the relative positions of the markers will change if the panel is imaged at an angle relative to the cover. Thus, a change in the relative positions of the markers can serve as a warning that the imaging angle has changed. Monitoring of this angle is important as the location of the target internal body lumen is also displaced from the gauge, and will therefore move relative to the gauge when the imaging angle changes.

Figure 2:
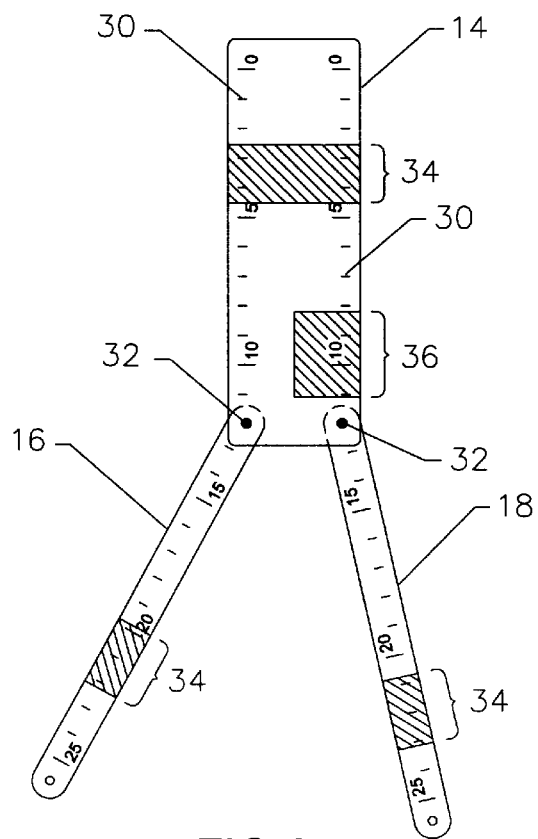
FIG. 2 illustrates the articulated gauge portions of the device of FIG. 1, the gauge portions including measurement scales which extend across the joints between the articulated portions and target deployment ranges within which an endoluminal prosthesis may be aligned.

The first, second, and third gauge portions are shown in isolation in FIG. 2. Each gauge portion includes a body of radiotranslucent material. A radiopaque scale 30 is imposed on these radiotranslucent bodies, with the scale preferably extending from the first gauge portion 14 to each of the second and third gauge portions 16, 18. Hence, the scales will generally pass through the pivot joints 32 connecting these gauge portions. Such continuous scales facilitate measurement along curving lumenal bodies when each gauge portion is substantially aligned along the adjacent axis of the body lumen. It is also possible to make use of scales which flex laterally rather than at a single hinge point to more accurately measure curving lumens. Hinge points, living hinges, flexible gauge bodies, articulated gauge bodies, or some other deformable structure may be used to provide at least one degree of freedom between the gauge portions. Regardless of the specific gauge structure, it is particularly preferred that the present guide have first and second gauge portions which can move relative to each other so as to effectively model the range of geometric shapes which a flexible or semi-flexible endoluminal prosthesis might assume when implanted. By overlaying a gauge with this geometric modeling capability directly over the target body lumen, the final deployed geometry of the prosthesis can be accurately estimated. Parallax indicators 29 can be placed at only one position, or at a number of positions as shown. Reference numerals along each scale give some indication of the absolute size of features aligned with the gauge. However, it should be remembered that the body features imaged through the gauge will often curve or angle relative to the panel 12.

The bodies of the first, second, and third gauge portions may conveniently be formed from a radiotranslucent polymer such as acrylic. Conveniently, existing radiopaque scale tapes, which are often affixed to a table surface prior to a fluoroscopically directed internal surgery, may be applied to the polymer gauge bodies to provide the radiopaque scales of the present invention. Such a tape is sold under the tradename LeMaitre Glow 'N Tell Tape, commercially available from Vascutech, Inc. The hinge points may comprise simple metallic screws or bolts connecting the substantially rigid gauge portions. Advantageously, such metallic bolts or screws are highly visible under fluoroscopy, thereby giving a further reference marker for positioning of the gauges.

The first, second, and third gauge portions further include radiopaque markings 34 identifying acceptable prosthetic end position ranges. End markers 34 will, in some embodiments, reflect the overall geometry of the prosthesis to be deployed with the assistance of the guide of FIG. 1. Alternatively, the end markers may be tailored to the individual patient, reflecting the range of safe deployment positions within which an end of the prosthesis will securely anchor to the surrounding luminal wall without covering any of the adjacent branching arteries. Hence, the guide may be included in a prosthesis kit, or end markers 34 may alternatively be positioned on the gauge portions before the deployment procedure begins, typically based on data provided by earlier computer tomography (CT), ultrasound, intravascular ultrasound (IVUS), or from direct luminal measurements using the methods and devices of co-pending U.S. patent application Ser. Nos. 08/380,735, and 08/435,288.

A prosthetic overlap range marker 36 is also illustrated in FIG. 2. Overlap marker 36 is particularly beneficial when assembling prostheses in situ, typically for treating a vascular aneurysm which spans a bifurcation. Overlap marker 36 indicates the minimum and maximum allowable overlap during assembly of such prosthetic modules.

Figure 3:
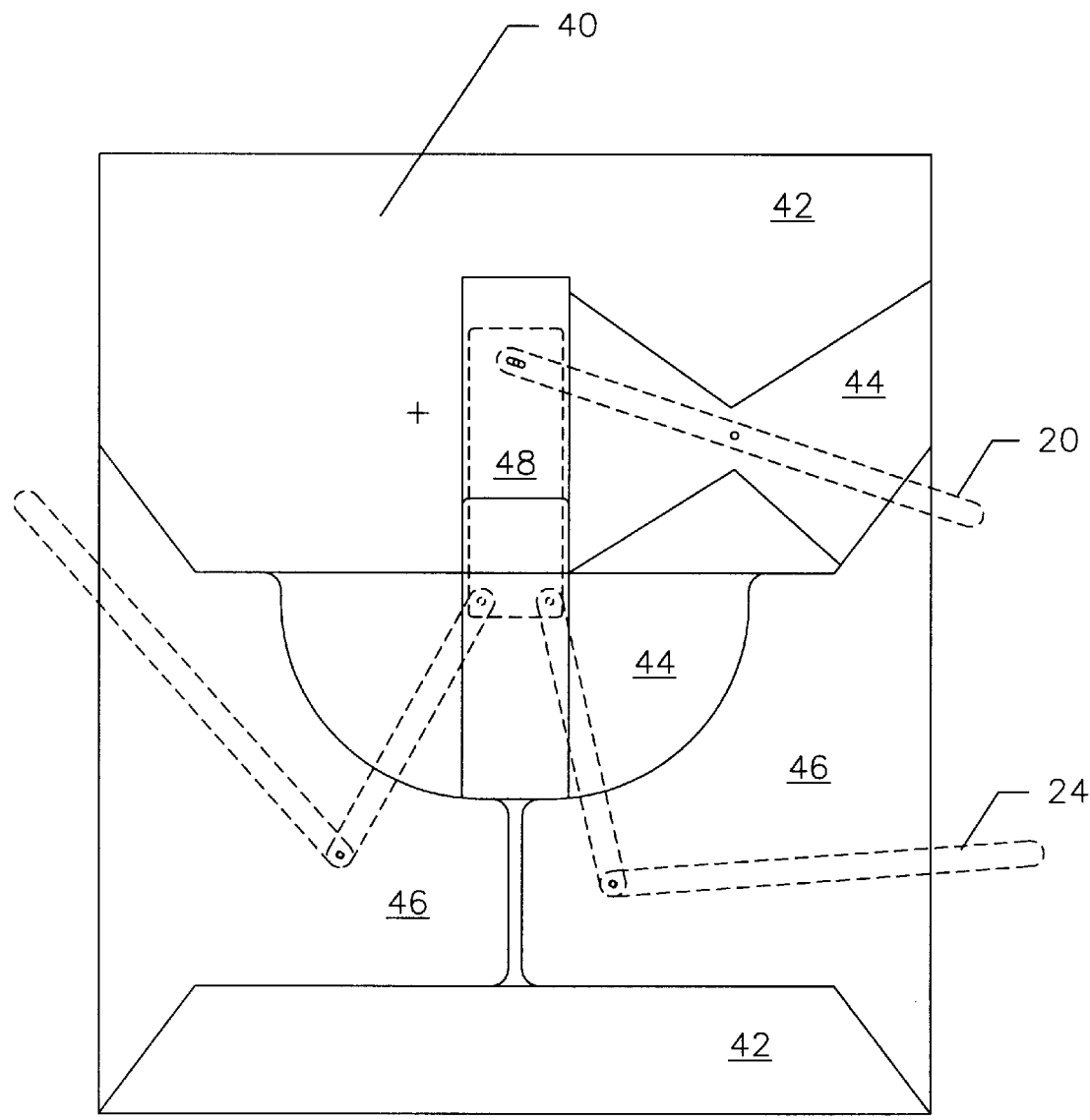
FIG. 3 illustrates the multi-level panel structure of the device of FIG. 1.

Referring now to FIG. 3, panel 12 includes a plate 40 which has been selectively machined to allow controlled movement of the first, second, and third gauge portions within specific, ranges. Plate 40 comprises a radiotranslucent material, generally being a polymer, and ideally being a high strength plastic such as a polycarbonate. Plate 40 is substantially planar, much of plate 40 retaining its full initial thickness 42 so as to support a cover thereon. Plate material has been removed to varying depths from selected areas 44, 46, and 48, to accommodate the various gauge portion bodies, levers, pivot connectors, and radiopaque marker tapes. In the embodiment shown, plate 40 is roughly 18 inches long and 15 inches wide, and comprises a polycarbonate with a thickness of between 0.25 and 1.0 inch. Material has been removed from areas 44, 46, and 48, at depths of about 0.085 inches, 0.15 inches, and 0.17 inches, respectively. These depths accommodate gauge portions and levers of 1/16 inch thick acrylic.

Figure 4A:
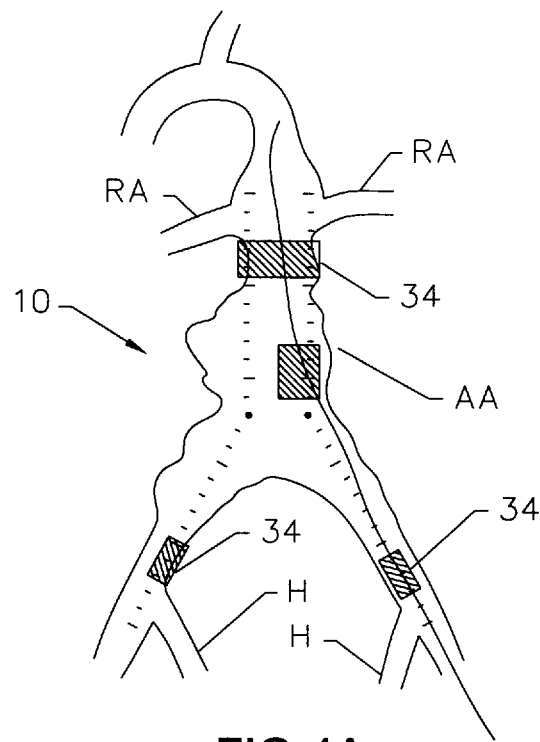
FIGS. 4A and B illustrate positioning and sizing of the device of FIG. 1 prior to prosthetic deployment, and also illustrate how the gauge may be used as a guide during positioning and deployment of an endoluminal prosthesis, particularly when the fluoroscopic image of the actual vascular system is difficult to interpret.

Referring now to FIGS. 4A and B, the size, position, and geometric layout of the guide may be established based on computer tomography, ultrasound, and direct lumenal measurements, as well as on fluoroscopy while a contrast agent is present in the target portion of the vascular system. When all this information is combined, it is possible to accurately size and position the guide prior to prosthetic deployment.

To align the fluoroscopic image of guide 10 along the vessels of the aortoiliac junction, the panel 12 will generally be positioned adjacent the surface of an operating table. Optionally, the panel is simply placed on top of a radiotranslucent table. Alternatively, the panel may be supported under the table, or inset into the table to avoid discontinuities in the operating surface. Regardless, the major surface of the panel is substantially aligned with the table surface, and the patient is positioned over the table and panel.

The patient and panel are radiographically imaged together using standard fluoroscopic equipment. For the embodiment shown in FIG. 1, the panel is moved laterally relative to the patient (and/or the imaging scope is moved relative to both) to align the axis of the first gauge portion with the lumenal axis of the abdominal aorta AA. Once the image of the first gauge portion appears to be coaxial with the aorta, the first lever is manipulated to bring the hinge points into the desired position along the lumenal axis. The first gauge portion may then be locked in position by advancing the wedge into engagement with the panel (see FIG. 1).

The second and third gauge portions are then aligned along the axis of the first and second iliac arteries I1, I2, respectively. Once again, the levers are locked into positions with wedges. It may take multiple iterations to align the guide, and alignment may be facilitated or verified by direct endoluminal measurement devices, by ultrasound or IVUS, by release of a contrast medium into the bloodstream, or the like. Once guide 10 is properly positioned, these additional imaging aids can dissipate or be removed without impairing the surgeons ability to direct the prosthetic deployment.

Figure 4B:
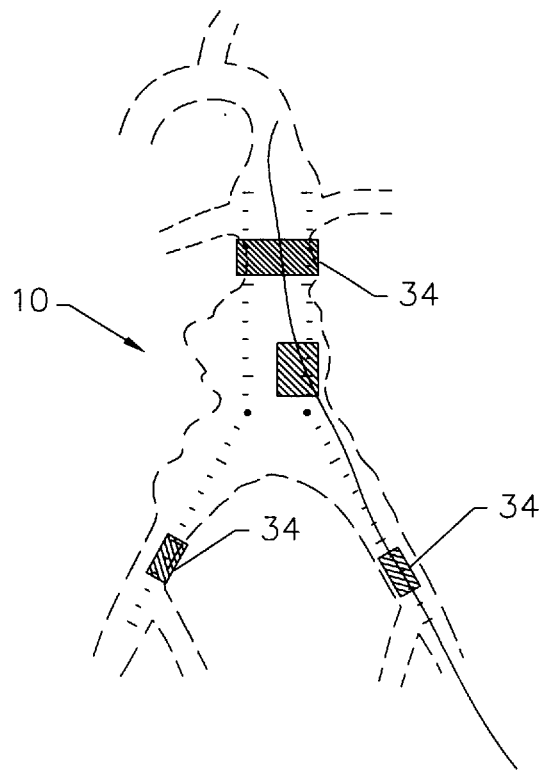

The fluoroscopic images provided during prosthetic deployment are not always as clear as might be desirable, as is schematically illustrated in FIG. 4B. Advantageously, the fluoroscope image of the pre-positioned and pre-sized deployment guide 10 facilitates accurate and safe positioning of the prosthesis spanning the aortic aneurysm AA without blocking of the renal arteries RA, or hypogastric arteries H. Hence, the articulated gauge of the present invention avoids uncertainties during the deployment process.

Figure 5:
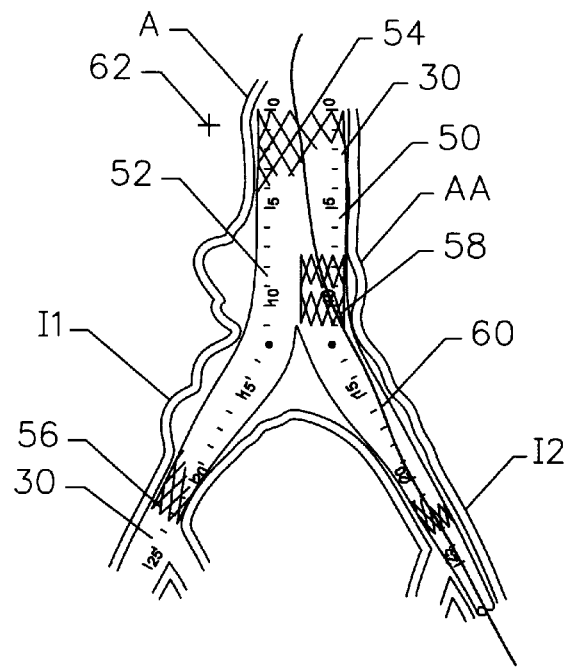
FIG. 5 illustrates the use of the device of FIG. 1 to fluoroscopically direct the in situ assembly of a bifurcated endoluminal prosthesis, according to the principles of the present invention.

FIG. 5 illustrates the use of the scale to assist in situ assembly of a modular bifurcated prosthesis 50. Bifurcated prosthesis 50 includes a peg-leg structure 52 having a trunk lumen end 54, a branch lumen end 56, and a port 58 therebetween. This peg-leg structure is typically deployed extending from the abdominal aorta A to one of the two iliac arteries I1. To complete isolation of abdominal aorta AA, a branch prosthetic module 60 is deployed extending from port 58 to the second iliac artery I2.

In the method illustrated in FIG. 5, allowable prosthetic positions for the ends and port are read off the numerical scale 30 of guide 10. Similarly, the allowable overlap may also be read by noting the final location of port 58 relative to the scale, and inserting branch prosthetic module 60 beyond that point within a known overlap range. While such methods provide great flexibility, allowing the surgeon to modify the procedure as the deployment unfolds, they may also be somewhat more susceptible to miscalculations during surgery. Hence, end range markings 34 and overlap range markers 36 as illustrated in FIG. 2 are generally preferred.

Figure 6:
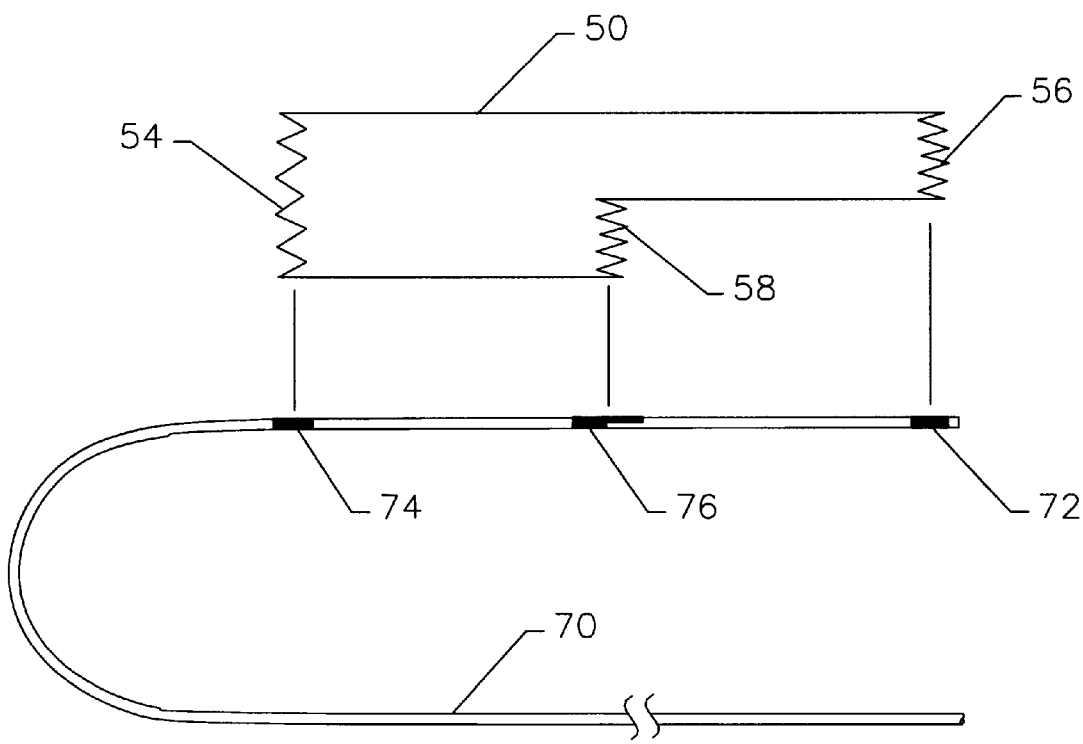
FIG. 6 illustrates a measurement verification catheter having position indicating markers which correspond to the ends and branch of a bifurcated endoluminal prosthesis, according to the principles of the present invention.

Referring now to FIG. 6, the present invention further provides a simple measurement confirmation catheter 70. Catheter 70 includes a distal marker 72, a proximal marker 74, and a branch marker 76. These markers are generally radiopaque, and are separated by distances which correlate to the length of bifurcated prosthesis 50, and to the axial location of port 58. Confirmation catheter 70 will generally be both smaller and more flexible than the delivery catheter used in deployment of bifurcated prosthesis 50. Once prosthesis 50 has been selected, and prior to its deployment, confirmation catheter 70 may be easily and atraumatically advanced over an access guidewire to ensure that the length and branch position of the chosen bifurcated prosthesis is appropriate for that particular patient. While the confirmation catheter illustrated in FIG. 70 is configured for a superior approach (as the branch end marker is nearest the distal portion of the catheter), such confirmation catheters may easily be adapted for inferior approaches, and may utilize a wide variety of alternative catheter structures.

Figure 7:
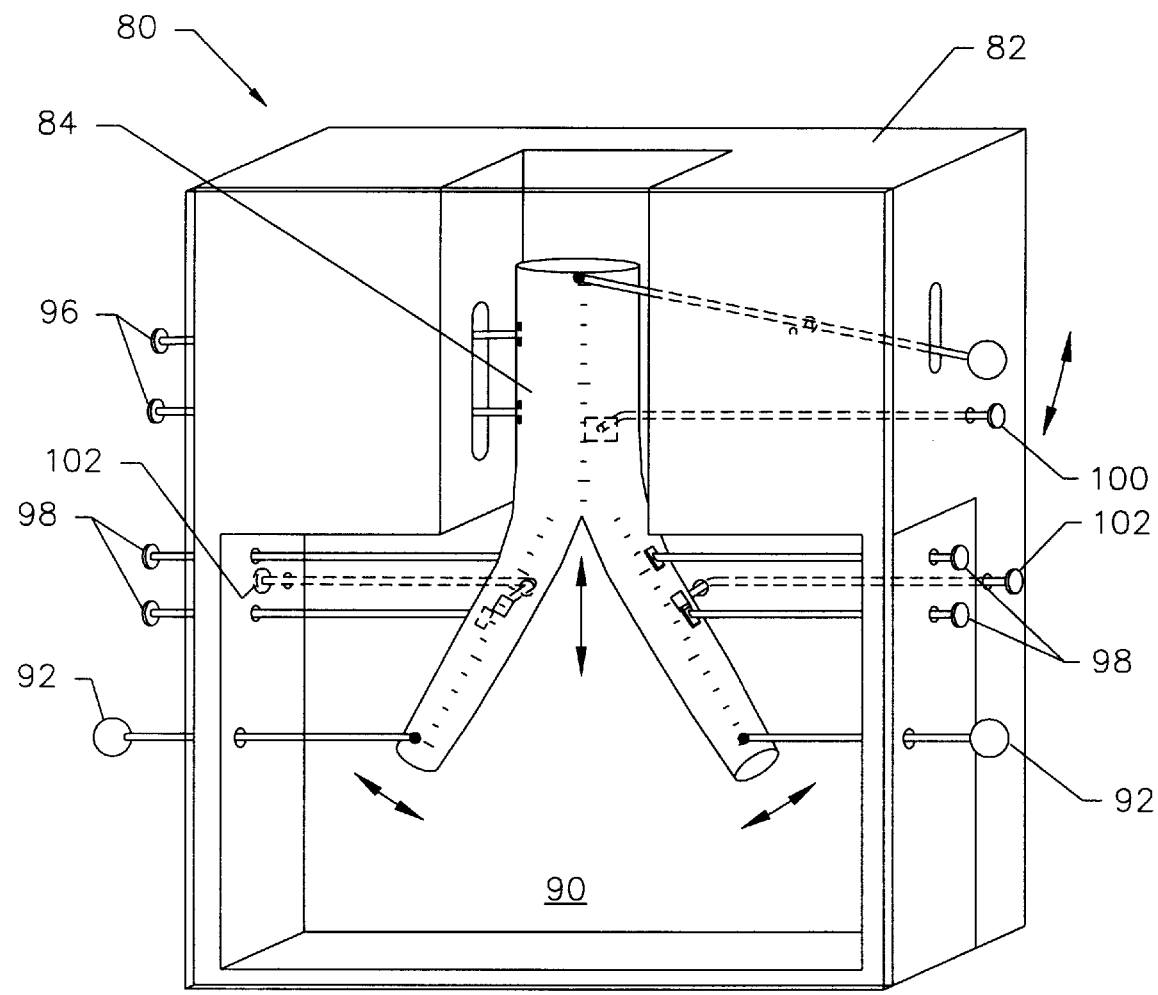
FIGS. 7–7B illustrate a three dimensional guide for modeling the geometry of a deployed endoluminal prosthesis, according to the principles of the present invention.
Figure 7A:
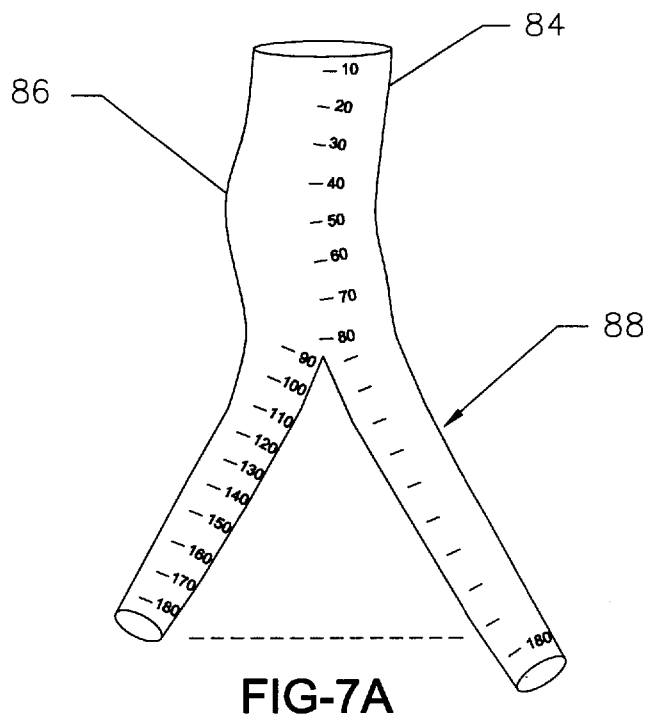
Figure 7B:
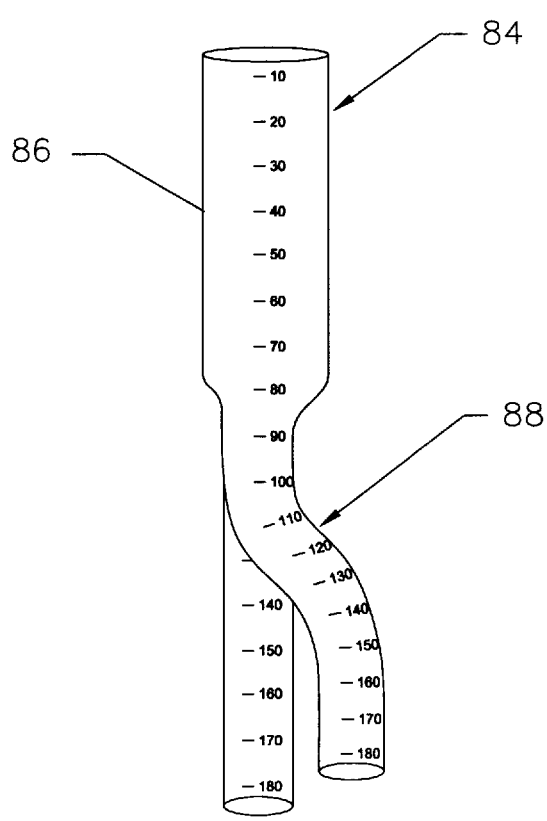

Referring now to FIGS. 7 through 7B, a three dimensional guide 80 includes a deep panel 82 and a three dimensional gauge 84. Three dimensional gauge 84 comprises a distortable body having a trunk portion 86 from which branch portions 88 extend. The trunk and branch portions are flexible, malleable, or formed from a series of articulatable elements or modules, allowing the branch portions to move laterally relative to the trunk portion. Hence, the trunk and branch portions can be used as the gauge portions in the method described above.

The flexibility of three dimensional gauge 84 structure also allows the surgeon to model the effects of the tortuosity of the individual body lumens on the final deployed shape of a bifurcated prosthesis. Lateral distortion of trunk portion 86 (as shown in FIG. 7A) models the effects of medial-lateral tortuosity of the proximal neck and body of an aortic aneurysm on the deployed prosthesis. Distortion of branch portion 88 normal to the cover models anterior-posterior tortuosity of the iliac arteries, as shown in FIG. 7B. Similarly, lateral deformation of the branch portions models medial-lateral iliac tortuosity. Modeling of anterior-posterior tortuosity of the aorta (not shown) may be particularly advantageous, as significant axial bends in this plane have been encountered, for example, where the aorta follows the curvature of the spine associated with lumbar lordosis. Lumenal bending can have a significant effect on lumenal axial position relative to a planar model, as can be understood with reference to the front view of FIG. 7A and the side view of FIG. 7B. Variations in lumenal geometries, and flexible prostheses which adapt to these geometries, are described in co-pending U.S. patent applications Ser. No. 08/615,697, filed Mar. 13, 1996, the full disclosure of which is incorporated herein by reference.

To take advantage of the flexibility of three dimensional gauge 84, deep panel 82 allows distortion of the trunk portion and the branch portions along the plane of cover 0, and also normal to cover 90, as well as providing lateral deflection of the branch portions. Specifically, lever 94 axially positions three dimensional gauge 84 and levers 92 laterally adjust the branches, as described above. Lead screws 96 also adjust the trunk portion to model medial-lateral tortuosity of the aorta, while lead screws 98 adjust for medial-lateral tortuosity of the iliac arteries.

Lead screw 100 lifts trunk portion 86 to adjust the gauge for anterior-posterior tortuosity of the aorta, while lead screws 102 lift the branch portions 88 adjust for similar tortuosity of the iliac arteries. For modeling of more complex curves, more than one lifting lead screw may be used on each portion.

The three dimensional gauge itself may comprise a malleable polymer based material, or may comprise a tube filled with gel. Alternatively, gel may be disposed within the layers of the tubing for flexibility and hoop strength. Radiopaque markers in the form of a reference scale (as shown) and/or target position ranges (as described above) will typically be included on both the trunk and branch portions of the gauge. The deep panel structure may be analogous to panel 12 of FIGS. 1 and 3, but will generally have greater thickness to allow the three dimensional gauge to distort therein when modeling tortuosity normal to the cover.

These exemplary embodiments have been described in some detail by way of illustration and example. A wide variety of alternative structures are also possible within the scope of the present invention. For example, the reference scale on the second or third gauge portions may be axially adjustable. This would allow the scale to reflect the actual deployment position of the port of a bifurcated peg-leg prosthetic structure. In some embodiments, it may be possible to have an additional side gauge portion supported by a side panel extending vertically from one edge of the panel, so that vertical angularity or curvature of the body lumen may be accurately modeled. As still further modifications and variations will be obvious to those of skill in the art, the scope of the present invention is limited solely by the appended claims.

What is claimed is:

1. A position guide for reference to internal anatomical features of a patient body, the guide comprising:
    a panel which defines a reference plane, the panel comprising a radiotranslucent material for imaging of the patient body therethrough;
    a first gauge portion supported by the panel, the first gauge portion having radiopaque markings; and
    a second gauge portion extending from the first gauge portion, the second gauge portion having radiopaque markings and being movable relative to the first gauge portion along the reference plane;
    wherein the markings of the first gauge portion define an axis, and wherein the second gauge portion is laterally deflectable relative to the gauge axis so that the markings of the first and second gauge portions are alignable along axially curving anatomical features; and
    wherein said guide further comprises a third gauge portion extending from the first gauge portion, the third gauge portion laterally deflectable relative to the first gauge portion axis independently of the second gauge portion so that the markings of the second gauge portion so that the markings of the second and third gauge portions are alignable along branching anatomical features.

2. A position guide for reference to internal anatomical features of a patient body, the guide comprising:
    a panel which defines a reference plane, the panel comprising a radiotranslucent material for imaging of the patient body therethrough;
    a first gauge portion supported by the panel, the first gauge portion having radiopaque markings; and
    a second gauge portion extending from the first gauge portion, the second gauge portion having radiopaque markings and being movable relative to the first gauge portion along the reference plane;
    wherein the markings of the first gauge portion define an axis, and wherein the second gauge portion is laterally deflectable relative to the gauge axis so that the markings of the first and second gauge portions are alignable along axially curving anatomical features; and
    wherein the second gauge portion rotatably engages the first gauge portion.

3. A position guide for reference to internal anatomical features of a patient body, the guide comprising:
    a panel which defines a reference plane, the panel comprising a radiotranslucent material for imaging of the patient body therethrough;
    a first gauge portion supported by the panel, the first gauge portion having radiopaque markings; and
    a second gauge portion extending from the first gauge portion, the second gauge portion having radiopaque markings and being movable relative to the first gauge portion along the reference plane;
    wherein the first gauge portion is slidable relative to the panel along the reference plane.

4. A position guide for reference to internal anatomical features of a patient body, the guide comprising:
    a panel which defines a reference plane, the panel comprising a radiotranslucent material for imaging of the patient body therethrough;
    a first gauge portion supported by the panel, the first gauge portion having radiopaque markings; and
    a second gauge portion extending from the first gauge portion, the second gauge portion having radiopaque markings and being movable relative to the first gauge portion along the reference plane;
    wherein the panel has a major surface which is substantially aligned with the reference plane and disposable adjacent the patient body and said positionguide further comprising a mechanism for moving the second gauge portion relative to the first gauge portion from a minor surface of the panel adjacent the major surface.

5. A fluoroscopic guide for a curving body lumen, the guide comprising:
- a panel having a major surface defining a reference plane and an edge adjacent the major surface, the panel comprising a radiotranslucent material;
- a first gauge portion supported by the panel, the first gauge portion having radiopaque markings which define an axis;
- a second gauge portion extending from the first gauge portion, the second gauge portion having radiopaque markings and being laterally deflectable along the reference plane relative to the axis of the first gauge portion; and
- a deflecting mechanism extending from the second gauge portion to the edge of the panel for aligning the markings of the first and second gauge portions along the curving body lumen while the body lumen is imaged through the panel.

6. A curving lumen guide as claimed in claim 5, wherein the first gauge portion is axially slidable relative to the panel.

7. A curving lumen guide as claimed in claim 6, further comprising a third gauge portion extending from the first gauge portion, the third gauge portion having radiopaque markings and being laterally deflectable along the reference plane relative to the axis of the first gauge portion independently of the second gauge portion.

8. A curving lumen guide as claimed in claim 7, wherein the deflecting mechanism comprises a first mechanical linkage extending between second gauge portion and the edge, a second mechanical linkage for axially sliding the first gauge portion and a third mechanical linkage for axial aligning the markings of the third gauge portions along the curving body lumen.

9. A curving lumen guide as claimed in claim 7, wherein the markings of the gauge portions comprise acceptable position ranges for positioning ends of a bifurcated endoluminal prosthesis.

10. A method comprising:
- imaging a vascular system of a patient body through a panel disposed adjacent the patient body;
- aligning markings of a first gauge portion on the panel with a first target site of the vascular system;
- aligning markings of a second gauge portion on the panel with a second target site of the vascular system, wherein a vascular axis at the first target site is disposed at an angle relative to a vascular axis at the second target site, and wherein the markings of the first and second gauge portions substantially indicate an axial length along the vascular system between the first and second target sites.

11. A method as claimed in claim 10, further comprising aligning markings of a third gauge portion on the panel with a third target site of the vascular system which is disposed at an angle relative to the first target site so that the markings of the first and third gauge portions indicate an axial length along the vascular system between the first and third target sites.

12. A method as claimed in claim 11, further comprising deploying a branching endoluminal prosthesis between the first, second, and third sites while imaging the vascular system through the panel, the first site being disposed along a trunk vessel and the second and third sites being disposed along branch vessels off the trunk vessel.

13. A position guide for reference to internal anatomical features of a patient body, the guide comprising:
- a panel which defines a reference plane, the panel comprising a radiotranslucent material for imaging of the patient body therethrough;
- a first gauge portion supported by the panel, the first gauge portion having radiopaque markings;
- a second gauge portion extending from the first gauge portion, the second gauge portion having radiopaque markings and being movable relative to the first gauge portion along the reference plane; and
- a parallax indicator having a first radiopaque marker at a first distance from the reference plane and a second radiopaque marker at a second distance from the reference plane.

* * * * *

UNITED STATES PATENT AND TRADEMARK OFFICE
CERTIFICATE OF CORRECTION

PATENT NO.    : 6,097,978
DATED         : August 1, 2000
INVENTOR(S)   : Demarais et al.

It is certified that error appears in the above-identified patent and that said Letters Patent is hereby corrected as shown below:

Column 10, claim 1,
Lines 14-15, the phrase "so that the markings of the second gauge portion" should be deleted.

Column 10, claim 4,
Line 64, "postionguide" should be replaced by -- position guide --.

Signed and Sealed this

Twenty-sixth Day of March, 2002

Attest:

JAMES E. ROGAN
*Attesting Officer*   *Director of the United States Patent and Trademark Office*